(12) United States Patent
Lafleche

(10) Patent No.: US 9,089,462 B1
(45) Date of Patent: Jul. 28, 2015

(54) PRESSURE ULCER MANAGEMENT PAD

(75) Inventor: Patrick Lafleche, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 285 days.

(21) Appl. No.: 13/987,302

(22) Filed: Jul. 5, 2012

(51) Int. Cl.
*A61G 7/057* (2006.01)
*A61F 7/08* (2006.01)
*A47C 21/04* (2006.01)

(52) U.S. Cl.
CPC . *A61G 7/057* (2013.01); *A61F 7/08* (2013.01); *A47C 21/042* (2013.01)

(58) Field of Classification Search
CPC .................. A61F 7/00; A61F 7/08; A47C 21/042–21/044; A61G 7/057
USPC ............ 5/421, 422, 652.2, 655.5, 655.9, 284; 607/96, 104
See application file for complete search history.

(56) References Cited

U.S. PATENT DOCUMENTS

| | | | | |
|---|---|---|---|---|
| 3,681,797 A | * | 8/1972 | Messner | .................. 297/180.13 |
| 4,108,146 A | * | 8/1978 | Golden | ......................... 607/104 |
| 5,448,788 A | * | 9/1995 | Wu | .................................... 5/421 |
| 5,486,206 A | | 1/1996 | Avery | |
| 5,643,336 A | | 7/1997 | Lopez-Claros | |
| 5,894,615 A | * | 4/1999 | Alexander | ......................... 5/421 |
| 6,402,775 B1 | | 6/2002 | Bieberich | |
| 6,653,607 B2 | * | 11/2003 | Ellis et al. | ..................... 219/528 |
| 6,699,266 B2 | | 3/2004 | Lachenbruch et al. | |
| 6,764,502 B2 | * | 7/2004 | Bieberich | ..................... 607/104 |
| 6,859,967 B2 | | 3/2005 | Harrison et al. | |
| 8,499,389 B2 | * | 8/2013 | Kirchhoff | ......................... 5/697 |
| 2010/0212088 A1 | * | 8/2010 | Deighan | ......................... 5/421 |

OTHER PUBLICATIONS

PCT International Search Report regarding Application No. PCT/US2013/048916 filed Jul. 1, 2013, a counterpart to U.S. Appl. No. 13/987,302.
PCT International Written Opinion regarding Application No. PCT/US2013/048916 filed Jul. 1, 2013, a counterpart U.S. Appl. No. 13/987,302.

* cited by examiner

*Primary Examiner* — Michael Trettel
(74) *Attorney, Agent, or Firm* — Warner Norcross & Judd LLP

(57) ABSTRACT

A temperature management pad includes a patient facing side, a cushioning layer for supporting the patient facing side above a surface, a cooling component located in, on, or adjacent the cushioning layer for cooling the patient facing side of the pad for cooling a patient lying thereon, wherein the cooling component includes a conduit formed between the patient facing side and the cushioning layer for circulating fluid through the pad across the cushioning layer. The cushioning layer comprises a gel cushioning layer with a continuous upper surface supporting the patient facing side, which includes channels formed therein. The conduit is supported in the channels for circulating fluid laterally across the gel cushioning layer and through the pad.

21 Claims, 3 Drawing Sheets

PRESSURE ULCER MANAGEMENT PAD

TECHNICAL FIELD AND BACKGROUND OF THE INVENTION

The present invention relates to a pad or overlay, and more particularly, a pad or overlay that is particularly suitable for use under a patient or invalid supported on a surface, such as on a cushion or mattress, in a hospital or other patient care facility, including long term care facilities or the like.

When patients are hospitalized or bedridden for any significant amount of time, patients can develop pressure sores or ulcers. These pressure sores or ulcers can be exacerbated by the patient's own poor circulation, such as in the case of diabetic patients, but typically form as a result of prolonged immobility, which allows the pressure exerted on the patient's skin from the mattress to decrease circulation in the patient's tissue. In addition to reducing circulation in the patients' tissue, lack of mobility can also cause heat and moisture build-up at the point of contact with the mattress. Heat contributes to the moisture build-up, which can cause maceration in the skin—which makes the skin more permeable and vulnerable to irritants and stresses, such as stresses caused by pressure or by shear, for example when a patient is moved across a mattress. It has been found with the same pressure an increase in skin temperature can cause an increase in tissue damage.

To address some of these issues, some beds incorporate a low air loss system, which directs air to the patient/mattress interface to reduce moisture. However, these systems tend to be position dependent and are not adjustable.

Accordingly there is a need for surface that can at least reduce the heat build up that can occur at the interface between the supporting surface and the patient's skin.

SUMMARY OF THE INVENTION

The present invention provides a temperature management pad that cools a patient's skin when the patient is lying on top of the pad. Optionally, the pad is independent of and sized to be smaller in one or more dimensions than the underlying support surface so that it can be moved for better alignment with the areas of the patient's body that are more vulnerable, which are patient dependent.

In one form of the invention, a temperature management pad includes a patient facing side, a cushioning layer, and a cooling layer. For example the cooling layer may comprise a fluid conduit for circulating fluid through the pad across the cushioning layer adjacent the patient facing side, which is a configured so that when a patient is lying on the patient facing side of the pad and over the fluid conduit the conduit will not be occluded by the weight of the patient.

In another form of the invention, a temperature management pad includes a patient facing side, a cushioning layer supporting the patient facing side above a surface, and a fluid conduit between the patient facing side and the cushioning layer for circulating fluid, such as cooled liquid, including cooled water and optionally water with fluorocarbons, through the pad across the cushioning layer. The cushioning layer is a configured so that when a patient is lying on the patient facing side of the pad and over the fluid conduit the conduit will not be occluded by the weight of the patient.

In yet another form of the invention, a temperature management pad includes a patient facing side, a cushioning layer supporting the patient facing side above a support surface, and a fluid conduit formed between the patient facing side and the cushioning layer for circulating fluid, such as cooled liquid, through the pad across the cushioning layer. The cushioning layer is adapted to at least reduce (1) shear between the patient facing layer and the support surface on which the pad is supported or (2) pressure on the patient's skin.

According to another form of the invention, a temperature management pad includes a patient facing side, a gel cushioning layer supporting the patient facing side above a support surface, a fluid conduit between the patient facing side and the cushioning layer for circulating cooled fluid through the pad across the cushioning layer. The gel cushioning layer has a continuous upper surface for supporting the patient facing side, with channels formed therein for locating the fluid conduit.

In any of the above pads, the patient facing side is formed by a patent facing layer, with the fluid or liquid conduit formed in the patient facing layer. For example, the patient facing layer may be formed by a film, such as a flexible polymeric film, including a polyester and polyether polyurethane film, a polyvinylchloride (PVC) film, a neoprene film, or a polyethylene film. Optionally, the patient facing layer is formed by at least two films, which are joined together to form the fluid or liquid conduit.

In any of the above pads, the cushioning layer includes a support surface facing side and a plurality of walls at the support facing side for supporting the pad on the support surface. For example, the walls may be configured to locally buckle under a pressure of a predetermine magnitude.

In a further aspect, the walls intersect to form a grid.

In yet another aspect, in any of the pads, the cushioning layer may comprise foam, gel, or a plurality of air bladders.

In any of the above pads with a gel layer, the gel layer may comprise a structural gel or a flowable gel, including a flowable gel with a plurality of spherical bodies.

According to yet another form of the invention, a temperature management pad includes a gel cushioning layer having a continuous upper surface for supporting a patient above a support surface and a cooling layer, such as a fluid conduit.

In one aspect, the gel cushioning layer includes a support surface facing side and a plurality of walls at the support facing sides for supporting the pad on the support surface. For example, the walls may be configured to locally buckle under a pressure of a predetermine magnitude.

In any of the above pads, the cushioning layer may include a plurality of channels at its continuous upper surface for locating a plurality of fluid conduits. Further, in any of the above pads, the pad may include an inlet conduit for fluid communication with fluid supply tubing and an outlet conduit, with the inlet conduit directing fluid to one or more of the plurality of the fluid conduits, and the outlet conduit receiving fluid from one or more of the plurality of the fluid conduits for discharge or recirculation through the pad.

In yet another form of the invention, a method of reducing pressure ulcer formation on a patient's skin includes supporting a patient on a mattress or cushion, suspending the patient's skin above the surface of the mattress or cushion, and cooling the interface between the patient's skin and the mattress or cushion.

For example, in any of the above pads or methods, the temperature of the cooled fluid or cooling component or device may be less than 30 degrees Celsius, less than 29 degrees Celsius, less than 28 degrees Celsius, less than 27 degrees Celsius, less than 26 degrees Celsius, less than 25 degrees Celsius, less than 24 degrees Celsius, less than 23 degrees Celsius, less than 22 degrees Celsius, less than 21 degrees Celsius or less than 20 degrees Celsius, including as low as 15 degrees Celsius. Optionally, the cooled fluid may be in a range of about 30 degrees Celsius to 15 degrees Celsius, in a range of about 28 degrees Celsius to 18 degrees Celsius, or in a range of about 26 degrees Celsius to 21 degrees Celsius.

According to another aspect, in any of the above pads or methods, the cooled fluid or cooling component or device induces a minimum temperature change at the skin of the patient of about 10 degrees Celsius, of about 8 degrees Celsius, of about 5 degrees Celsius, of about 3 degrees Celsius.

In a further aspect, the method may also include reducing pressure and/or shear between the patient's skin and the mattress or cushion.

Accordingly, the present invention provides a pad that is configured to cool a patient's skin while not significantly, if at all, interfering with the pressure redistribution by, shear reduction by, and/or immersion of a patient into the underlying support surface.

These and other objects, advantages, purposes, and features of the invention will become more apparent from the study of the following description taken in conjunction with the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE PREFERRED EMBODIMENTS

Figure 1:
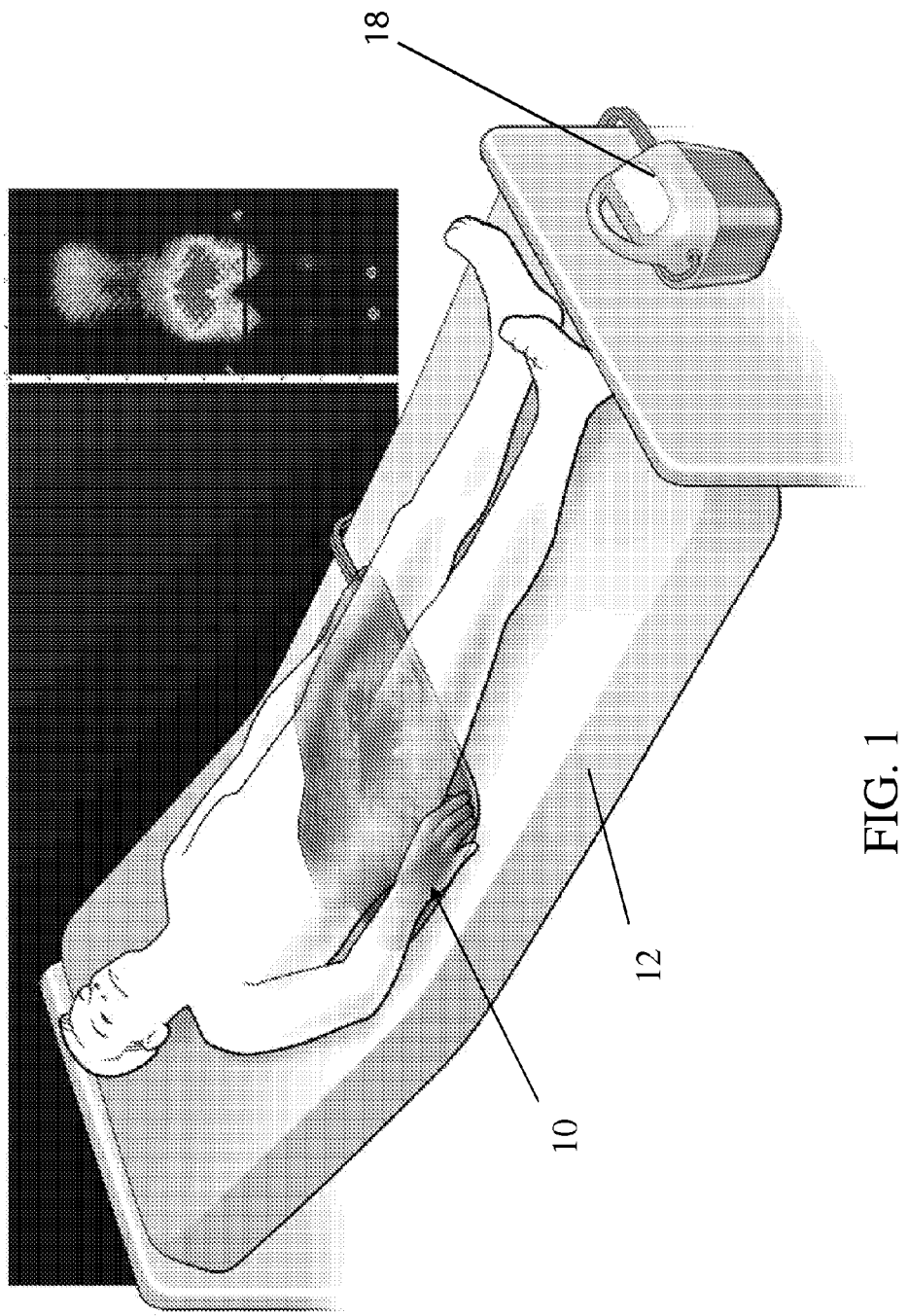
FIG. 1 is a perspective view of a pad of the present invention on a bed supporting a patient.

Referring to FIG. 1, the numeral 10 generally designates a pad of the present invention that is configured for use on a mattress 12 and under a patient P, for example under the sacral region of a patient, and to circulate cooling fluid under the patient to cool the skin of the patient. While illustrated as being used under the sacral region of a patient, it should be understood that pad 10 may also be used (and optionally reconfigured) for use under other regions of a patient's body, such as the heels. As will be more fully described below, pad 10 may be configured to provide shear reduction and/or pressure redistribution that supplements the shear reduction and/or pressure redistribution characteristics of an underlying mattress, such as a mattress for a hospital bed. For details of a suitable mattress and/or bed, reference in made herein to the mattresses and beds described in U.S. Pat. Nos. 8,006,332; 7,690,059; 7,805,784; 7,962,981; 7,861,334; 6,843,873; 7,730,566; 7,823,233; 7,823,234; 7,827,636; 5,088,136; 5,325,551, and 5,542,136 and U.S. copending application Ser. No. 13/022,326, filed Feb. 7, 2011, entitled PATIENT/INVALID HANDLING SUPPORT; U.S. copending application Ser. No. 13/022,372, filed Feb. 7, 2011, entitled PATIENT INVALID HANDLING SUPPORT; U.S. copending application Ser. No. 13/022,382, filed Feb. 7, 2011, entitled PATIENT INVALID HANDLING SUPPORT; U.S. copending application Ser. No. 13/022,454, filed Feb. 7, 2011, entitled PATIENT INVALID HANDLING SUPPORT; U.S. copending application Ser. No. 12/640,770, filed Dec. 17, 2009, entitled PATIENT SUPPORT; and U.S. copending application Ser. No. 12/640,643, filed Dec. 17, 2009, entitled PATIENT SUPPORT, all commonly owned by Stryker Corporation of Kalamazoo, Mich., which are herein incorporated by reference in their entireties. Reference is also made to U.S. Pat. Nos. 5,749,111; 6,026,527; 6,197,099; 6,413, 458; 6,865,759; 7,060,213 and 8,075,981 for examples of suitable mattresses constructed of structural gel, which are all incorporated herein by reference in their entireties.

Figure 2:
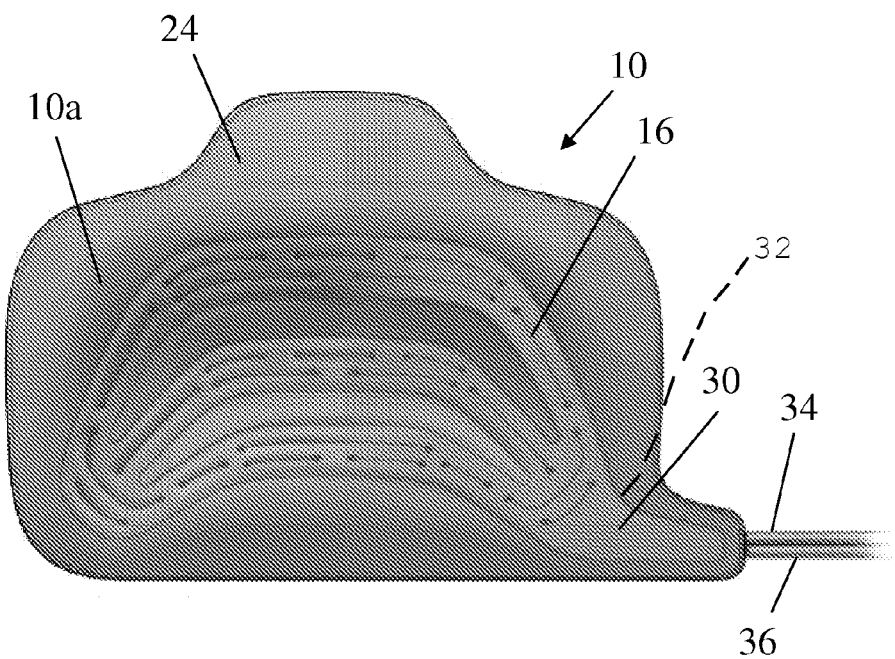
FIG. 2 is a top plan view of the pad of FIG. 1 with the top layer removed to show a flow path through the pad.
Figure 3:
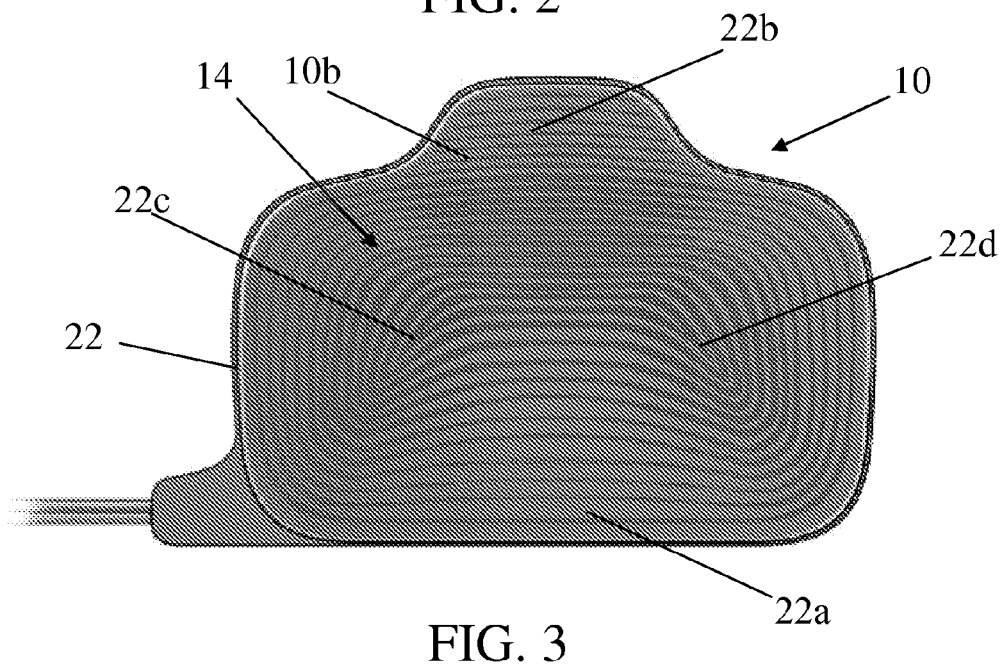
FIG. 3 is a bottom plan view of the pad of FIG. 2.

Referring to FIGS. 2 and 3, the pad 10 includes a cushioning layer 14 and one more conduits 16 for circulating fluid, such as cooled liquid including cooled water and optionally water with fluorocarbons, through pad 10 to cool a patient's skin or tissue lying on the pad. Conduits 16 are in fluid communication with a pump 18 (see FIG. 1), which circulates a fluid, such as water, through the conduits 16 in pad 10. For an example of a suitable pump, reference is a pump sold under the trademark T/PUMP® by Stryker Corporation of Kalamazoo, Mich. The pump and any supporting control system may be mounted in the mattress itself, such as described in U.S. Pat. Nos. 5,325,551, and 5,542,136, both commonly owned by Stryker Corporation of Kalamazoo, Mich., or may be located external to the mattress as shown, for example at the footboard or the side rail, or at other locations on or off the bed, including an on-board pump, such as disclosed in U.S. Pat. No. 8,011,039, commonly owned by Stryker Corporation of Kalamazoo, Mich., all of which are herein incorporated by reference in their entireties.

Cushioning layer 14 may be formed from a variety of different materials and structures to provide shear reduction and/or localized pressure management. For example, cushioning layer 14 may comprise a gel cushioning layer 20. Suitable gelatinous elastomeric materials for forming the gel layer may be formed by blending an A-B-A triblock copolymer with a plasticizer oil, such as mineral oil. The "A" component in the A-B-A triblock copolymer is a crystalline polymer like polystyrene and the "B" component is an elastomer polymer like poly(ethylene-propylene) to form a SEPS polymer, a poly (ethylene-butadyene) to form a SEBS polymer, or hydrogenated poly(isoprene+butadiene) to form a SEEPS polymer. For examples of suitable gelatinous elastomeric materials, the method of making the same, and various suitable configurations for the gel layer reference is made to U.S. Pat. Nos. 3,485,787; 3,676,387; 3,827,999; 4,259,540; 4,351, 913; 4,369,284; 4,618,213; 5,262,468; 5,508,334; 5,239,723; 5,475,890; 5,334,646; 5,336,708; 4,432,607; 4,492,428; 4,497,538; 4,509,821; 4,709,982; 4,716,183; 4,798,853; 4,942,270; 5,149,736; 5,331,036; 5,881,409; 5,994,450; 5,749,111; 6,026,527; 6,197,099; 6,843,873; 6,865,759; 7,060,213; 6,413,458; 7,730,566; 7,823,233; 7,827,636; 7,823,234; and 7,964,664, which are all incorporated herein by reference in their entireties.

Other formulations of gelatinous elastomeric materials may also be used in addition to those identified in these patents. As one example, the gelatinous elastomeric material may be formulated with a weight ratio of oil to polymer of approximately 3.1 to 1. The polymer may be Kraton 1830 available from Kraton Polymers, which has a place of business in Houston, Tex., or it may be another suitable polymer. The oil may be mineral oil, or another suitable oil. One or more stabilizers may also be added. Additional ingredients such as, but not limited to, dye or microspheres may also be added. In another example, the gelatinous elastomeric material may be formulated with a weight ratio of oil to copolymers of approximately 2.6 to 1. The copolymers may be Septon 4055 and 4044 which are available from Kuraray America, Inc., which has a place of business in Houston, Tex., or it may be other copolymers. If Septon 4055 and 4044 are used, the weight ratio may be approximately 2.3 to 1 of Septon 4055 to Septon 4044. The oil may be mineral oil and one or more stabilizers may also be used. In addition to these examples, as well as those disclosed in the aforementioned patents, still other formulations may be used.

Referring to FIG. 3, in the illustrated embodiment, cushioning layer 14 includes a plurality of ribs or walls 22, which are nested and, further, are sized such that when a load, such as a patient's weight, is placed on the patient facing side of the pad 10a, the walls will buckle to prevent bottoming-out of the upper surface 24 of the pad to the upper surface of the underlying mattress. Even when fully buckled or folded, the material forming the walls will thereby provide cushioning to the patient.

Optionally, walls 22 may be arranged in closed nested loops 22a and rows 22b, with rows 22b extending between opposed edges of the pad adjacent the outermost wall of loops 22a. In the illustrated embodiment, pad 10 includes a generally rectangular shaped pad with rounded edges and with an optional enlarged lobed region 10b so that the pad focuses cooling on the sacrum, trochanter and ischium regions of the patient. As shown, rows 22 extend across the enlarged lobed region in a generally parallel relationship and are optionally evenly spaced.

As best seen in FIG. 3, loops 22a have regions of generally parallel wall sections and also include wall sections that form tightly nested regions 22c and 22d which generally correspond to the boney protuberances of the hip of a patient where the pressure exerted by a patient lying on the pad is likely to be the greatest.

Alternately, cushioning layer 14 may be formed from a foam material or may be formed from a plurality of bladders. For examples of suitable construction of air support bladders for forming the cushioning layer reference is made to U.S. pending patent application Ser. No. 12/640,770 filed Dec. 17, 2009, entitled PATIENT SUPPORT; Ser. No. 12/640,643 filed Dec. 17, 2009, entitled PATIENT SUPPORT; Ser. No. 13/022,326 filed Feb. 7, 2011, entitled PATIENT/INVALID HANDLING SUPPORT; Ser. No. 13/022,372 filed Feb. 7, 2011, entitled PATIENT/INVALID HANDLING SUPPORT; Ser. No. 13/022,382 filed Feb. 7, 2011, entitled PATIENT/INVALID HANDLING SUPPORT; and Ser. No. 13/022,454 filed Feb. 7, 2011, entitled PATIENT/INVALID HANDLING SUPPORT, all commonly owned by Stryker Corporation of Kalamazoo, Mich., which are herein incorporated by reference in their entireties. It should be understood that the height and optionally the width of the bladders would be scaled down to fit into the pad application, where the overall height of the pad is optionally maintained at 2 inches or less, more typically 1 inch or less. Alternately, the bladders may have a tubular construction, which laterally extend across the width of the pad.

Figure 4:
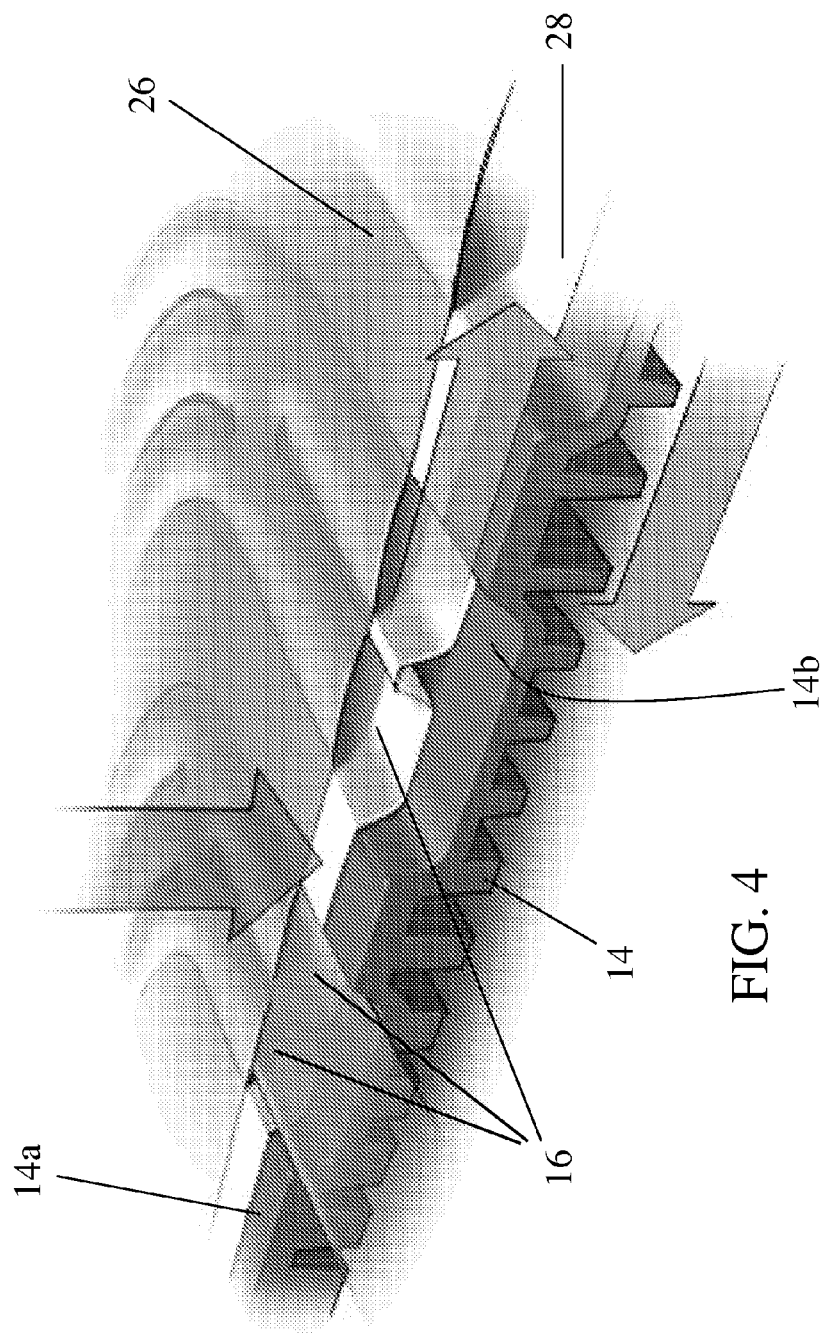
FIG. 4 is a cross-section view through the pad.

Referring to FIG. 4, cushioning layer 14 optionally includes a solid or continuous upper surface 14a that includes one or more channels 14b formed therein. Channels 14b support and located the conduits 16 in the upper surface of the cushion so that when a patient is lying on the pad, the cushion layer will support the patient rather than the conduits so that the patient's weight will not occlude the conduits, which instead will be redistributed to the downwardly facing walls of the cushioning layer.

Referring again to FIG. 4, conduits 16 are formed between two sheets of flexible material, such as two sheets of flexible film, including thermoformed plastic film, which for the patient facing side of the pad. For example, suitable films may be formed from PVC, polyurethane (PU), polyethylene (PE), polyester polyurethane (PPU) film, neoprene film, or thermapolyurethane film. Suitable polyurethane films may have a relatively low durometer, which results in the film exhibiting supple qualities and can feel very soft against human skin. Further, the elongation properties of polyurethane films are especially desirable and allow the film to significantly stretch to thereby reduce the shear stresses on a patient supported on pad 10.

For example, the upper film 26 and lower film 28 may be joined together, for example, by welding, at discrete locations to thereby form the conduit(s) 16 between the sheets. Given their elongation and flexibility characteristics, as best seen in FIG. 4, films 26 and 28 will generally follow the surface topology of upper portion 14a of cushioning layer 14 so that the conduits 16 are recessed into the channels 14b formed in upwardly facing side 14a of cushioning layer 14. Optionally when films 26 and 28 are joined together film 28 is provided with some slack or excess material so that it will balloon away from film 26 when channel 16 is filled with fluid. In this manner, even when channels 16 are inflated, upper film 26 will retain a generally flat configuration though the regions directly over the passageways may form slightly raised regions, such as shown in FIG. 4. In this manner, as described above, cushioning layer 14 will provide support to the conduits so that when a patient is lying on pad 10, the patient's weight will not occlude the conduits so that cooling fluid will continue to flow through the pad.

Referring again to FIG. 2, conduits 16 extend to the edge of pad 10, where they merge into an inlet conduit 30 and an outlet conduit 32, which are respectively in fluid communication with supply tubing 34, which extends to pump 18 for circulating the cooling fluid to the pad, and with discharge tubing 36 that returns fluid to the pump 18 for cooling and recycling back to the pad (for example in a closed loop system). Optionally, conduits 16 expand as they extend through the pad, which reduces the back pressure on the fluid as it flows through the various passageways. In some instances when dealing with heavier patients, the fluid may need to be pressurized to a higher range, and/or the size and number of the conduits and/or thickness of the pad may need to be increased to avoid occlusion of the conduits.

Alternately or in addition, pad 10 may incorporate one or more cooling components. For example, pad 10 may incorporate an electric or electronic device or a phase change material. For example, a layer of phase change material with a removable film may be applied above or adjacent the cushion layer which could be activated by removal of the film, which exposes the phase change material to air and causes the material to become cool. In another embodiment, the phase change material layer is activated by allowing an internal sack or region in the layer to break or open allowing two chemicals to combine which cause the phase change reaction. Further, the layer may be removable so that when the phase change reaction is complete or not longer generates sufficient cooling that it can be replaced.

Alternately, a semiconductor device, such as a Peltier effect device, may be embedded or applied to the upwardly facing surface, which is powered either directly through wiring or a conductive fabric or inductively powered by a transmitter adjacent the pad. When energized, the device draws energy from the interface between the patient and the pad to thereby reduce the temperature of the patient's skin cells.

In yet another embodiment, pad 10 may incorporate one or more conductive fabric layers, such as aluminum, stainless steel, silver or copper, which are in communication with one or more cooling devices, such as described above, that are located for example along the edge or end of the pad, which cool the layer(s) by conduction, which in turn then cools the interface between the patient and the pad. The silver and copper fabric then have the added benefit of providing antimicrobial properties.

As noted above, fluid conduit or the cooling component or device may be extended through pad 10 transversely across the cushioning layer to cool the patient's skin or tissue. For example, in order reduce the likelihood of damage or degree of damage to the patient's skin due to pressure exerted on the patient's skin by simply lying on a mattress, it is desirable to cool the patient's skin or tissue below 32 degrees Celsius, including temperatures below 31 degrees Celsius, below 30 degrees Celsius, below 29 degrees Celsius, below 28 degrees Celsius, below 27 degrees Celsius, below 26 degrees Celsius, and below 25 degrees Celsius. For example, to cool the skin to the above noted temperatures, the temperature of the cooled fluid may be less than 30 degrees Celsius, less than 29 degrees Celsius, less than 28 degrees Celsius, less than 27 degrees Celsius, less than 26 degrees Celsius, less than 25 degrees Celsius, less than 24 degrees Celsius, less than 23 degrees Celsius, less than 22 degrees Celsius, less than 21 degrees Celsius, or less than 20 degrees Celsius, including as low as 15 degrees Celsius. Optionally, the cooled fluid may be in a range of about 30 degrees Celsius to 15 degrees Celsius, in a range of about 28 degrees Celsius to 18 degrees Celsius, or in a range of about 26 degrees Celsius to 21 degrees Celsius.

Alternately or in addition, the cooled fluid or cooling component or device induces a minimum temperature change at the skin of the patient of about 10 degrees Celsius, of about 8 degrees Celsius, of about 5 degrees Celsius, or of about 2 or 3 degrees Celsius.

To increase the heat transfer to the fluid, the volume of fluid flowing through or the size of the cooling component or device the pad may be varied. Further, the heat transfer rate is optimally sufficient to cool the patient's skin or tissue locally and but not sufficient to cool the patient's core body temperature or at least to maintain the core body temperature within 1 to 3 degrees Celsius from the patient's normal core body temperature.

One of the goals is to cool the patient's skin sufficiently to reduce the metabolic rate of the patient's skin cells so that the need for nutrients is lowered. Another goal is to balance blood flow with the nutrient needs of the patient's skins cells. At lower temperatures, the skin cells may endure greater pressure without the attendant damage with the same pressure at higher temperatures. In other words, the lower the applied pressure, the warmer the patient's skin can be without creating tissue damage. Also, in the balance is the comfort to the patient. The cooler the skin, the more discomfort to the patient.

To monitor the heat transfer, pump 18 may include a control system with a sensor that measures the temperature of the supply fluid and a sensor that measures the discharge fluid temperature, which can be used to measure the thermal transfer and to adjust the temperature of the supply fluid if needed.

Depending on the specific application, the size of the pad may be varied. For example, for cooling the sacrum, trochanter and ischium regions the pad may have dimensions in a range of 36 to 18 in width and 24 to 18 in length, and have an overall thickness in a range of 2 inches to ½ inch or less.

While the pad is intended to be flexible and pliable and optionally stretchy enough to follow the surface topology of the mattress or cushion when a patient is lying on the pad, when in use, such as shown in FIG. 1, pad 10 remains unfolded to prevent inadvertent occlusion of the conduits. Further, the pad is intended to be flexible and optionally stretchy enough to avoid interfering with the pressure redistribution and immersion of the patient into the mattress beneath the pad and also without generating an increase in shear on the patient's skin.

Accordingly, the pads, described above, each reduce the temperature of the skin cells of the patient by conduction. Optimally the pads, described above, each cool the skin cells of the patient sufficiently to lower the metabolic rate of the skin cells of a patient to reduce, if not eliminate, damage to the skin cells when subject to pressures associated with lying on a mattress or cushion. Further, the pad is movable and adjustable so that it can be positioned to suit the needs of a given patient.

Directional terms, such as "upper" "lower" "top," "bottom," "inner," "inwardly," "outer" and "outwardly," are used to assist in describing the invention based on the orientation of the embodiments shown in the illustrations. The use of directional terms should not be interpreted to limit the invention to any specific orientation(s).

While several forms of the invention have been shown and described, other changes and modifications will be appreciated by those skilled in the relevant art. Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent The embodiments of the invention in which an exclusive property or privilege is claimed are defined as follows:

1. A temperature management pad comprising:
   a patient facing side;
   a cushioning layer for supporting said patient facing side above a surface;
   a cooling component located in, on, or adjacent said cushioning layer for cooling the patient facing side of the pad for cooling a patient lying thereon, wherein said cooling component includes a conduit formed between said patient facing side and said cushioning layer for circulating fluid through said pad across said cushioning layer;
   wherein said cushioning layer comprise a gel cushioning layer, said gel cushioning layer having a continuous upper surface supporting said patient facing side, and said continuous upper surface having channels formed therein, and
   said conduit supported in said channels for circulating fluid laterally across said gel cushioning layer and through said pad.

2. A temperature management pad according to claim 1, wherein said gel layer comprises a flowable gel.

3. The temperature management pad according to claim 2, wherein said flowable gel comprises a flowable gel with a plurality of spherical bodies.

4. A temperature management pad according to claim 1, wherein said patient facing side is formed from a film.

5. A temperature management pad according to claim 4, wherein said film comprises a flexible polymeric film, such as polyester and polyether polyurethane film.

6. The temperature management pad according to claim 5, wherein said flexible polymeric film comprises a polymeric film selected from the group consisting of polyester, polyether polyurethane film, PVC film, neoprene film, and polyethylene film.

7. The temperature management pad according to claim 4, wherein said film comprises a first film, further comprising a second film, said upper side of said gel layer supporting said second film to thereby form at least part of the cooling component, and said first film and said second film forming said cooling component.

8. A temperature management pad comprising:
   a patient facing side;
   a cushioning layer for supporting said patient facing side above a surface;
   a cooling component located in, on, or adjacent said cushioning layer for cooling the patient facing side of the pad for cooling a patient lying thereon; and
   wherein the cushioning layer includes a support surface facing side and a plurality of walls at said support facing side for supporting said pad on the surface.

9. A temperature management pad according to claim 8, wherein said walls are configured to locally buckle under a pressure of a predetermine magnitude.

10. A temperature management pad according to claim 9, wherein said walls intersect to form a grid.

11. A temperature management pad comprising:
    a patient facing side;
    a cushioning layer for supporting said patient facing side above a surface;
    a cooling component located in, on, or adjacent said cushioning layer for cooling the patient facing side of the pad for cooling a patient lying thereon;
    wherein said patient facing side is formed from a first film, said first film comprising a flexible polymeric film; and
    said patient facing side further comprising a second film, said films forming the boundaries of a conduit.

12. A temperature management pad according to claim 11, wherein said cushioning layer comprises a foam, gel, or a plurality of air bladders.

13. A temperature management pad according to claim 12, wherein said cushioning layer comprises gel.

14. A temperature management pad according to claim 13, wherein said gel comprises a structural gel.

15. A temperature management pad according to claim 11, wherein said second film comprises a flexible polymeric film.

16. The temperature management pad according to claim 15, wherein said second film comprises a polyester film, a polyether polyurethane film, a PVC film, a neoprene film, or a polyethylene film.

17. A temperature management pad according to claim 11, wherein said cushion layer includes a least one channel formed in the side of the cushion layer facing said second film wherein said second film extends into said channel.

18. A temperature management pad according to claim 11, wherein said cushioning layer at least partially prevents said conduit from being occluded by the weight of a patient supported on said pad.

19. The temperature management pad according to claim 11, wherein said first film comprises a polyester film, a polyether polyurethane film, a PVC film, a neoprene film, or a polyethylene film.

20. A temperature management pad comprising:
    a gel cushioning layer having a continuous upper surface for supporting a patient above a support surface;
    a conduit extending laterally across said gel layer for circulating fluid through said pad; and
    wherein said gel cushioning layer includes a support surface facing side and a plurality of walls at said support facing side for supporting said pad on said support surface.

21. A temperature management pad according to claim 20, wherein said walls are configured to locally buckle under a pressure of a predetermine magnitude.

* * * * *